United States Patent [19]
Stone et al.

[11] Patent Number: 6,020,383
[45] Date of Patent: Feb. 1, 2000

[54] METHOD FOR REDUCING BLOOD CHOLESTEROL AND/OR BLOOD TRIGLYCERIDES

[75] Inventors: William Lawrence Stone, Jonesborough; Andreas Micheal Papas, Kingsport, both of Tenn.

[73] Assignee: Eastman Chemicals Company, Kingsport, Tenn.

[21] Appl. No.: 09/228,092

[22] Filed: Jan. 11, 1999

[51] Int. Cl.[7] .................................................. A61K 31/05
[52] U.S. Cl. ........................................... 514/734; 514/824
[58] Field of Search ..................................... 514/734, 824

[56] References Cited

PUBLICATIONS

W. Stone, et al., *J. National Cancer Inst.,* 89:1006–1014, 1997.
G. Levine, et al., *New England Journal of Medicine,* 332:512–521, 1995.
Stone, et al., *Annals of Nutrition and Metabolism,* 30:94–103, 1986.
Mahley, et al., *PNAS USA,* 76:1746–1750, 1979.
Mahley, et al., *J. Lipid Research,* 18:314–324, 1997.
Haliwell, B., Murcia, M.A., Chirico, S., and Aruoma, O. (1995) "Free Radicals and Antioxidants in Food and in Vivo: What They Do and How They Work", Crit. Rev. Food Sci. Nutr. 35, 7–20.
Janero, J.M. (1995) "Ischemic Heart Disease and Antioxidants: Mechanistic Aspects of Oxidative Injury and its Prevention", Crit. Rev. Food Sci., Nutr. 35, 65–81.
Partnasarathy, S., Steinberg, D., and Witztum, J.L. (1992) "The Role of Oxidized Low–Density Lipoproteins in the Pathogenesis of Atherosclerosis", Rev. Med. 43, 219–225.
Papas, A.M. (1993) "Oil–Soluble Antioxidants in Foods", Toxicology and Industrial Health 9, 123–149.
CA 111:28578, Kaplan et al. Jan. 1989.

*Primary Examiner*—Kimberly Jordan
*Attorney, Agent, or Firm*—Cheryl J. Tubach; Harry J. Gwinnell

[57] ABSTRACT

Blood cholesterol and/or blood triglycerides are reduced in a mammalian subject by administering an effective amount of tert-butylhydroquinone or a salt thereof. The mammalian subject is preferably human. Additionally, a preparation of tert-butylhydroquinone in dosage unit form is provided to reduce blood cholesterol and/or blood triglycerides. The preparation is advantageously designed for oral administration.

7 Claims, No Drawings

METHOD FOR REDUCING BLOOD CHOLESTEROL AND/OR BLOOD TRIGLYCERIDES

FIELD OF THE INVENTION

The invention relates to health of the human body, and more particularly to a health body by the reduction of blood cholesterol and/or blood triglycerides.

BACKGROUND OF THE INVENTION

TBHQ (tert-butylhydroquinone, $C_{10}H_{14}O_2$, molecular weight 166.22, CAS No.1948-33-0) is a white to light tan crystalline solid phenolic antioxidant. Other major commercial phenolic antioxidants include butylated hydroxyanisole (BHA), butylated hydroxytoluene (BHT) and propyl gallate. TBHQ is approved in the United States for food use up to 200 mg/kg of fat or oil in the food (21 CFR 172.185). TBHQ primarily functions as a food antioxidant by inhibiting fatty acid oxidation. Such oxidation leads to the production of objectionable end products such as peroxides, aldehydes and ketones that impart offensive odor and taste to the food.

TBHQ has other uses as well. TBHQ is approved for use in cosmetics up to 0.1% of the product and as an inhibitor of polymerization of polyunsaturated polyesters including those in contact with food (Comestics Ingredients Review, 1986).

In W. Stone, et al., *J. National Cancer Inst.*, 89: 1006–1014, 1997, phenolic antioxidants have been reported as possibly reducing the risk of some forms of cancer, especially of the digestive system. However, high levels of BHA are suspected to cause forestomach carcinomas in rodents and high levels of BHT are suspected to cause liver cancers. TBHQ has exhibited no such carcinogenicity. Thus, a study to determine whether TBHQ reduces the risk of colon cancer was initiated. The results of this study prompted the discovery of the present invention, which has major health implications.

SUMMARY OF THE INVENTION

Quite unexpectedly, tert-butylhydroquinone (TBHQ) has been found to reduced blood cholesterol and triglycerides in the blood. The effect of which is to significantly reduce the risk of heart disease. Thus, the present invention is a method of reducing blood cholesterol and/or blood triglycerides in a mammalian subject. The method comprises the step of administering an effective amount of tert-butylhydroquinone (or a salt thereof) such that the level of blood cholesterol and/or blood triglycerides is reduced.

Another aspect of the present invention is a preparation of TBHQ in dosage unit form which can be administered to a subject to obtain a reduction in blood cholesterol and/or blood triglycerides. The preparation has from about 1 mg to about 150 mg of at least one compound selected from the group consisting of tert-butylhydroquinone and pharmacologically acceptable salts thereof, and a pharmaceutical diluent. Preferably, the dosage unit form is adapted for oral administration. In this regard, the dosage unit form can be a tablet, capsule, portion of food or drink, or a liquid.

DETAILED DESCRIPTION OF THE INVENTION

A study was conducted which focussed on the issue of whether tert-butylhydroquinone (TBHQ) reduces the risk of colon cancer. The results of that study prompted the unexpected discovery that TBHQ, when administered to a subject at a particular dosage level, has a blood cholesterol and/or blood triglyceride-reducing effect in the subject. This unexpected efficacy of reducing blood cholesterol and/or blood triglycerides of the present invention has major health implications.

Evidence is overwhelming that a direct association exists between high cholesterol and triglyceride levels and a significant increase in the risk of heart disease. In a proposed mechanism, cholesterol and triglycerides play a significant role in heart disease. Low density lipoprotein (LDL) primarily comprises cholesterol, cholesteryl ester and triglycerides. LDL undergoes oxidation and causes macrophage cells associated with the immune function to engulf it. Excessive production of oxidized LDL results in foam cells which are macrophages laden with oxidized LDL. Foam cells have very low mobility and, thereby, tend to accumulate on the artery wall and initiate atherogenesis by attracting leucocytes and platelets. This association is further confirmed in a report by G. Levine which indicated that reduction of blood cholesterol in humans by use of effective drugs reduced heart disease and mortality significantly (G. Levine, et al., *New England Journal of Medicine*, 332: 512–521, 1995).

The present invention provides a method of reducing blood cholesterol and/or blood triglycerides in a mammalian subject comprising the step of administering an effective amount of tert-butylhydroquinone (or a salt thereof) such that the level of blood cholesterol and/or blood triglycerides is reduced. The mammalian subject is preferably human.

The TBHQ is preferably administered in a dosage unit form having from about 1 mg to about 150 mg of a compound of TBHQ or its pharmacologically acceptable salts and a pharmaceutical diluent. More preferably, the dosage unit would be from about 3 mg to about 150 mg. Even more preferably, the dosage unit would be from about 15 mg to about 150 mg. For example, the TBHQ dose of 25.9 mg/kg of diet is equivalent to 25.9 mg/4490 kcal of diet. Assuming that this is directly extrapolated to humans consuming 3,000 kcal/day, the daily intake would be 17.3 mg/day. Since a wide effective range is known to exist for compounds that have biological activity, doses up to five fold lower and doses up to five fold higher are likely to be effective. The TBHQ dosage unit would typically be administered from once per day to up to three times a day.

The dosage unit is prepared by combining the TBHQ or its salt with non-toxic pharmaceutical diluents, which are well known in the art. The diluent may include solids or liquids, such as corn starch, lactose, sucrose, peanut oil, olive oil, sesame oil, and water. The diluent may also include foods fortified with TBHQ such as drinks, snacks, or other foods. Other diluents which may be used include lipophilic antioxidants, fish oils, or other edible oils. The concentration of the TBHQ in the diluent should exceed 200 ppm weight by weight.

The dosage unit may be incorporated into a number of different use formulations such as tablets or capsules containing TBHQ; foods fortified to supply TBHQ (drinks, snacks, other foods); and nutritional supplements fortified with TBHQ such as vitamin mineral capsules, antioxidant capsules, tablets or other formulations (powder, etc.). TBHQ may be used alone in these formulations or in combination with other synthetic and natural antioxidants such as BHA, BHT, propyl gallate, vitamin E, vitamin C, tocopherols, tocotrienols, beta-carotene, other carotenoids, phytochemicals, lipoic acid, isoflavones, coenzyme Q10, etc. When TBHQ is combined with a different antioxidant, the combined antioxidants may result in an additive or synergistic effect.

In a preferred embodiment, the invention is provided as a kit for orally administering a preparation in dosage unit form to obtain blood cholesterol and/or blood triglyceride-reducing effect. The kit comprises a dosage unit from about 1 mg to about 150 mg of at least one compound selected from the group consisting of tert-butylhydroquinone and pharmacologically acceptable salts thereof; a pharmaceutical diluent; and instructions for orally administering the preparation.

A description of the experimental work that led to the determination that TBHQ has blood cholesterol and/or blood triglycerides reducing effect is described below. Experiment 1 was conducted for the purpose of studying the potential influence of TBHQ on oxidative stress in the colon of rats. Experiment 1 unexpectedly found that dietary TBHQ reduced plasma levels of cholesterol and triglycerides. Experiment 2 was, therefore, conducted to determine if: (1) the results of Experiment 1, with respect to plasma-lipids, was reproducible; (2) TBHQ influenced plasma-lipids in a dose-dependent manner; and (3) BHT, an antioxidant similar to TBHQ, also lowered plasma-lipid levels.

EXPERIMENT 1

Rats (12/group) were fed a high fat semisynthetic diet (containing 15% corn oil stripped of tocopherol plus 1% cholesterol) containing all necessary nutrients as described by the National Research Council (NRC, 1978). Treatments evaluated consisted of the semisynthetic diet plus the following test agents: (1) Control (no test agent); (2) alpha-tocopherol, 0.156 mmol/kg of diet equivalent to 100 IU/kg; (3) gamma-tocopherol, 0.156 mmol/kg; (4) TBHQ, 0.156 mmol/kg equivalent to 25.9 mg/kg of diet.

Rats were fed these treatment diets for 12 weeks and then half of the rats in each group were switched to lower fat diets containing 5% corn oil and no cholesterol. Because rats consumed 11% more of the low fat diet to maintain the same caloric intake, the levels of nutrients and test agents were adjusted accordingly. Blood samples were collected after 24 weeks on the trial in tubes containing sodium EDTA as anticoagulant. Plasma separated from these blood samples was analyzed for cholesterol and triglycerides using standard commercial kits obtained from Sigma.

Quite unexpectedly, this study showed that TBHQ reduced blood cholesterol and triglycerides, especially in rats fed a high fat diet. Specifically, rats fed a high fat control diet without TBHQ had cholesterol levels of 79 mg/100 ml, while in the group fed the same diet, but supplemented with TBHQ, cholesterol was 44.6 mg/100 ml. The corresponding triglyceride values were 157.2 mg/100 ml and 39.1 mg/100 ml, respectively.

The effect of TBHQ was lower or absent in the low-fat diet. This is likely due to the fact that absorption of TBHQ is enhanced by fat. In addition, TBHQ could affect enzymatic action that is stimulated only by high fat in the diet. In this regard, the rat high fat diet of this example contains a caloric percentage derived from fat comparable to that of the typical human diet. As such, the rat low fat diet has limited relevance to human nutrition and its effects on plasma lipids.

EXPERIMENT 2

Sixty inbred Fisher-344 rats (12/dietary group) were fed a high fat semisynthetic diet containing 15% corn oil, 1% cholesterol, torula yeast, sucrose, and complete vitamin and mineral mix with selenium and supplemental methionine (since torula yeast is low in this amino acid). The rats were divided into dietary groups as follows:

(1) TBHQ at two doses (25 mg/kg diet or 200 mg/kg diet)
(2) BHT at two doses (25 mg/kg diet or 200 mg/kg diet)
(3) Control with no TBHQ or BHT.

The plasma cholesterol and plasma triglycerides were measured (using a standard enzymatic assay) in triplicate for each rat in two week intervals. The results are presented in Table 1 below.

TABLE 1

Change In Plasma Lipids Over Two Week Period

| Group | Cholesterol (mg/dl)* | Triglycerides (mg/dl |
|---|---|---|
| TBHQ-25 | $3.1^a$ | $-5.2^a$ |
| TBHQ-200 | $6.9^a$ | $5.9^a$ |
| BHT-25 | $18.5^b$ | $12.4^a$ |
| BHT-200 | $15.5^b$ | $38.7^b$ |
| Control | $8.0^a$ | $2.1^a$ |
| 2-Way Anova | | |
| Antioxidant | none, TBHQ, BHT | $p < 0.001$ |
| Dose | 0, 25, 200 | $p < 0.002$ |

*Column entries having different letters indicate that the entries are statistically different ($p < 0.05$).

The data in Table 1 support the following conclusions:
(1) BHT increases plasma levels of cholesterol and triglycerides in a rat model;
(2) TBHQ does not increase plasma cholesterol or triglycerides, and has a tendency to lower levels of these lipids; and
(3) TBHQ appears to be a better synthetic antioxidant than BHT from a cardiovascular disease standpoint.

While the study was carried out with rats, the findings apply to humans because the rat has been shown to be a good model for many conditions related to lipid metabolism and health. See, for example, Stone, et al., *Annals of Nutrition and Metabolism*, 30: 94–103, 1986, for a discussion of the use of a rat model to study the influence of dietary factors on plasma composition and for alterations in lipoprotein levels. See also Mahley, et al., *PNAS USA*, 76: 1746–1750, 1979, where the rat was used as a model in which to study the metabolism of human lipoproteins. Finally, see Mahley, et al., *J. Lipid Research*, 18: 314–324, 1997 that states that rats are particularly resistant to the development of hypercholesterolemia. In general, the effects of dietary factors or drugs that influence plasma cholesterol or triglyceride levels are greater in humans than rats. This suggests that the effects of TBHQ on lowering plasma cholesterol and/or triglycerides would be greater in humans than in rats because rats are a more stringent species.

The invention has been described in detail with particular reference to preferred embodiments thereof, but it will be understood that variations and modifications can be effected within the spirit and scope of the invention.

We claim:
1. A method of reducing blood cholesterol and/or blood triglycerides in a mammalian subject comprising the step of:
   administering an effective amount of tert-butylhydroquinone or a salt thereof such that the level of blood cholesterol and/or blood triglycerides is reduced.
2. The method of claim 1, wherein the tert-butylhydroquinone or the salt is administered in combina- tion with an antioxidant selected from the group consisting of BHA, BHT, propyl gallate, vitamin E, vitamin C, tocopherols, tocotrienols, beta-carotene, other carotenoids, phytochemicals, lipoic acid, isoflavones, coenzyme Q10, or mixtures thereof.

3. The method of claim 1, wherein prior to the step of administering, the tert-butylhydroquinone or the salt is combined with a pharmaceutical diluent.

4. The method of claim 3, wherein the concentration of the tert-butylhydroquinone in the diluent exceeds 200 ppm w/w.

5. The method of claim 1, wherein the amount of tert-butylhydroquinone is from about 1 mg to about 150 mg.

6. The method of claim 1, wherein the mammalian subject is a human.

7. The method of claim 1, wherein the form of the tert-butylhydroquinone is one of a tablet, capsule, food, liquid, or drink.

* * * * *

UNITED STATES PATENT AND TRADEMARK OFFICE
CERTIFICATE OF CORRECTION

PATENT NO. : 6,020,383
DATED : February 01, 2000
INVENTOR(S) : William Lawrence Stone and Andreas Michael Papas It is certified that error appears in the above-identified patent and that said Letters Patent is hereby corrected as shown below:

Title page, items
[75] Inventors, "Micheal" should read --Michael--

[73] Assignee, "Chemicals" should read --Chemical--

Signed and Sealed this

Fifth Day of December, 2000

Attest:

Attesting Officer

Q. TODD DICKINSON
Director of Patents and Trademarks

UNITED STATES PATENT AND TRADEMARK OFFICE
CERTIFICATE OF CORRECTION

PATENT NO. : 6,020,383
DATED : February 1, 2000
INVENTOR(S) : William Lawrence Stone and Andreas Michael Papas It is certified that error appears in the above-identified patent and that said Letters Patent is hereby corrected as shown below:

<u>Title page,</u>
Item [73], Assignee, "Eastman Chemical Company" should read -- East Tennessee State University --.

Signed and Sealed this

Twenty-ninth Day of April, 2003

JAMES E. ROGAN
*Director of the United States Patent and Trademark Office*